United States Patent [19]

Kambin

[11] Patent Number: 5,395,317
[45] Date of Patent: Mar. 7, 1995

[54] UNILATERAL BIPORTAL PERCUTANEOUS SURGICAL PROCEDURE

[75] Inventor: Parviz Kambin, Devon, Pa.

[73] Assignee: Smith & Nephew Dyonics, Inc., Andover, Mass.

[21] Appl. No.: 784,693

[22] Filed: Oct. 30, 1991

[51] Int. Cl.[6] ............ A61M 31/00; A61M 5/00; A61B 10/00

[52] U.S. Cl. .................. 604/51; 604/22; 604/116; 604/170; 128/753; 128/754; 128/DIG. 26; 606/61; 606/130

[58] Field of Search ............ 604/51, 116, 117, 170, 604/174, 22; 128/DIG. 26, 749–755, 898; 606/130, 61

[56] References Cited

U.S. PATENT DOCUMENTS

| | | | |
|---|---|---|---|
| 2,919,692 | 1/1960 | Ackermann | 128/754 |
| 3,017,887 | 1/1962 | Heyer | 604/174 X |
| 3,941,127 | 3/1976 | Froning | 604/116 X |
| 4,539,476 | 9/1985 | Sharpe | 128/754 X |
| 4,545,374 | 10/1985 | Jacobson . | |
| 4,573,448 | 3/1986 | Kambin . | |
| 4,638,799 | 1/1987 | Moore | 604/116 X |
| 4,678,459 | 7/1987 | Onik et al. . | |
| 4,750,487 | 6/1988 | Zanetti | 606/130 |
| 4,968,298 | 11/1990 | Michelson . | |
| 5,004,457 | 4/1991 | Wyatt et al. | 606/130 X |
| 5,047,036 | 9/1991 | Koutrouvelis | 606/130 |

FOREIGN PATENT DOCUMENTS 2234906  2/1991  United Kingdom .

OTHER PUBLICATIONS

Schreiber et al, Clin. Orth. Rel. Res., 283, Jan. 1989, pp. 35–42.

*Primary Examiner*—Randall L. Green
*Assistant Examiner*—Mary Beth Jones
*Attorney, Agent, or Firm*—Pravel, Hewitt, Kimball & Krieger

[57] ABSTRACT

A method of percutaneously emplacing at least two cannulae in a patient, such as for percutaneous decompression of a herniated disc, using a guide secured to one cannula to index a second cannula as it is percutaneously advanced into the body. The guide may take the form of jigs adapted to be secured to one cannula with bores arranged to slidingly receive a guidewire or a cannula.

8 Claims, 3 Drawing Sheets

FIG. 1
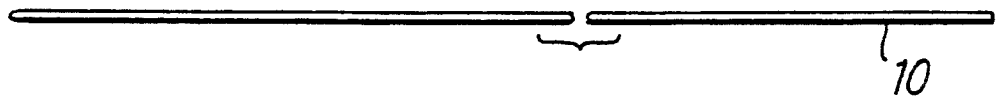
FIG. 2
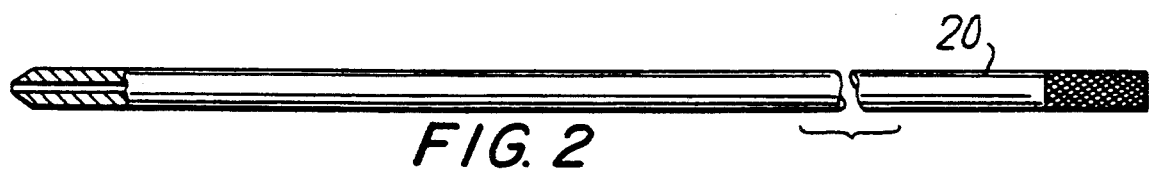
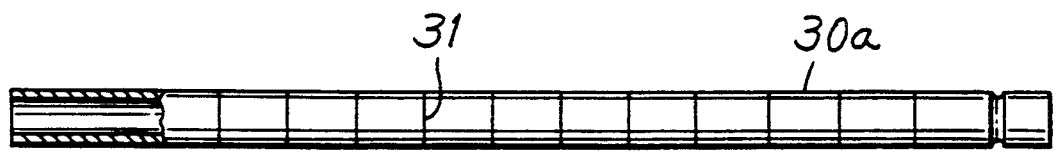
FIG. 3
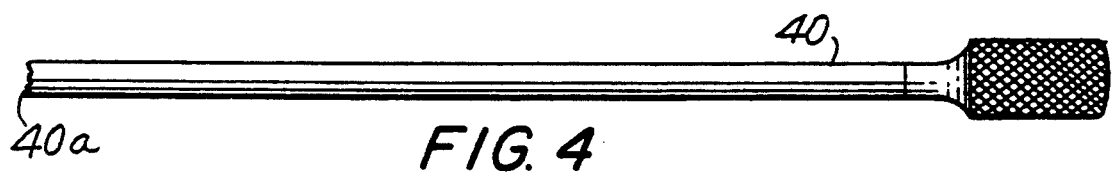
FIG. 4
FIG. 5
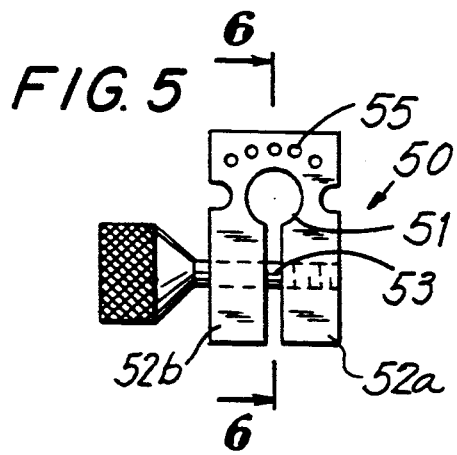
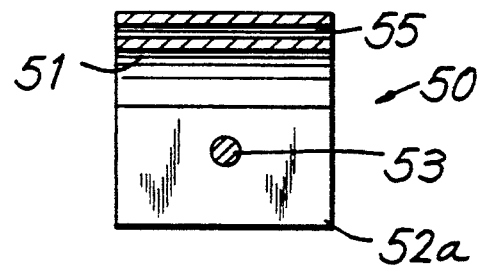
FIG. 6

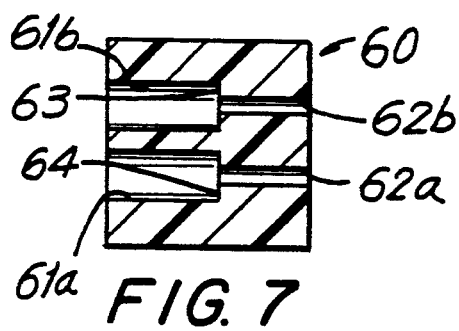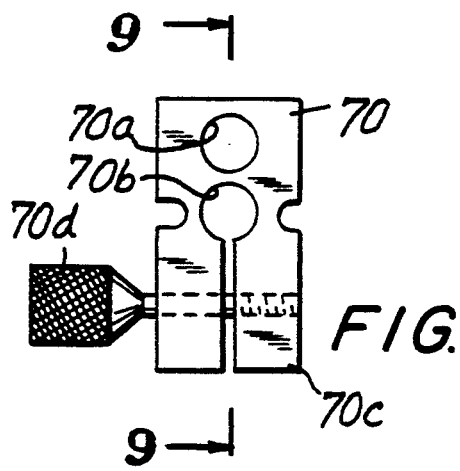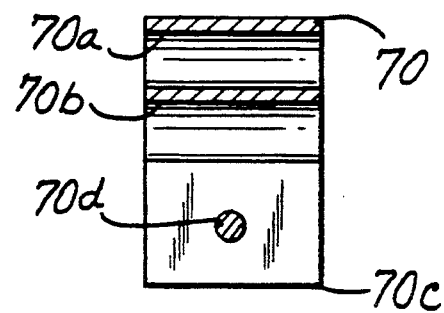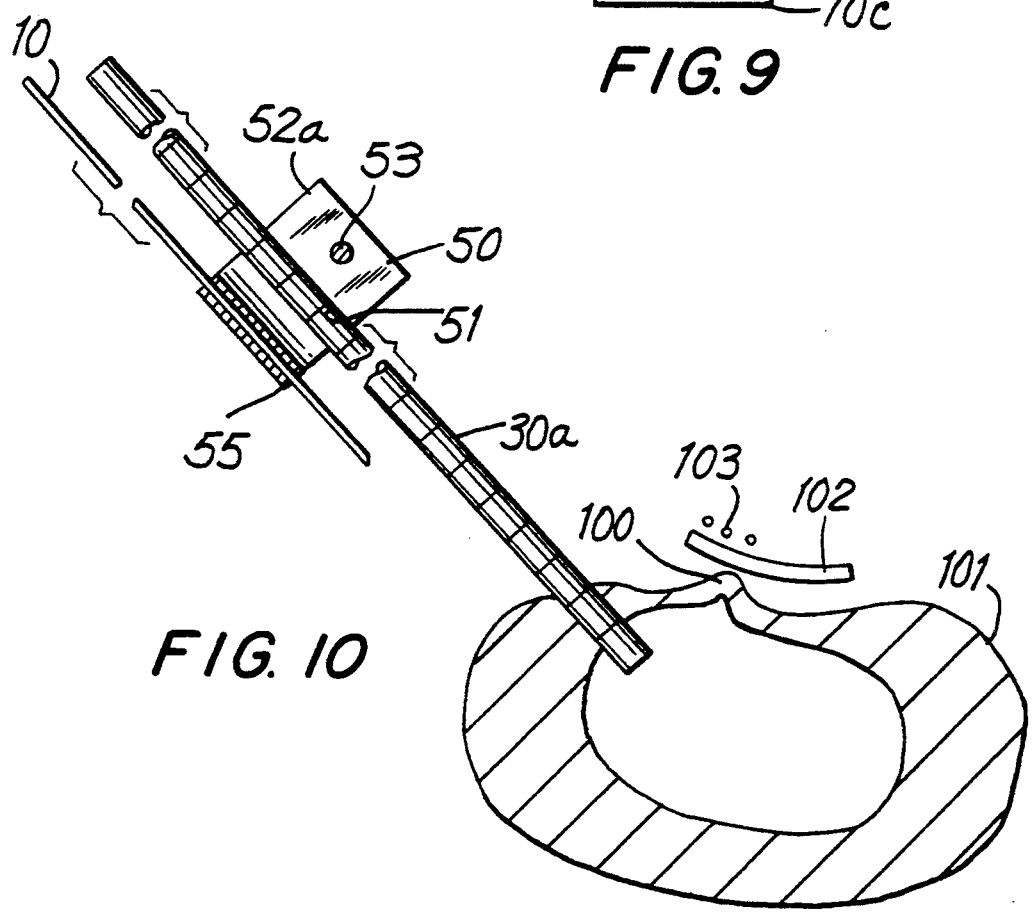

UNILATERAL BIPORTAL PERCUTANEOUS SURGICAL PROCEDURE

This invention relates to surgery and specifically to a novel method for accessing herniated intervertebral discs in a human patient.

Low back pain syndrome with sciatica secondary to herniated intervertebral discs represents a major health problem in the United States. An intervertebral disc is a structure which occupies the space between the vertebrae and acts, among other things, as a shock absorbing cushion. A normal disc consists of two parts: a central part known as the "nucleus" and a surrounding part known as the "annulus" or "annulus fibrosis". The annulus degenerates with age, as does the nucleus. Degeneration of the disc is characterized by collagenation, in which some of the fluid content of the nucleus is lost and fragments of collagenized fibrous tissue are formed which float in the tissue fluid. At this stage of degeneration, external forces can readily increase the hydrostatic pressure on the nucleus, causing the fibers of the annulus to rupture. Nucleus fragments protrude. This, in turn, may cause pressure on the adjacent nerve root with resultant pain. Degeneration of the disc may also be caused by other factors, for example, by accidental injury.

Several methods of treatment already exist. One method, usually referred to as "laminectomy" involves the surgical excision of the symptomatic portion of the herniated disc. This method of treatment has been used for many years, however, typical hospitalization time is nine days. Microsurgery has also been used in the treatment of herniated discs, in a procedure known as "microlumbar discectomy." This microsurgical procedure, although less invasive, nevertheless carries with it many of the complications associated with the older procedure, including injury to the nerve root and dural sac, perineural scar formation, reherniation at the site of the surgery, and instability due to excess bone removal. Another method of treatment is known as chemonucleolysis, which is carried out by injection of the enzyme chymopapain into the disc structure. This procedure has many complications including severe pain and spasm, which may last up to several weeks following injection. Sensitivity reactions and anaphylactic shock occur in limited but significant numbers of patients.

A further method of treatment, automated percutaneous lumbar discectomy, utilizes a specially designed needle which is inserted into a ruptured disc space. The nucleus of the disc is removed by suction instead of open surgery.

Another method of treatment is discussed in U.S. Pat. No. 4,573,448 and involves the percutaneous evacuation of fragments of the herniated disc through an access cannula positioned against the annulus of the herniated disc. A measure of safety and accuracy is added to this operative procedure by the arthroscopic visualization of the annulus and other important structures which lie in the path of the instruments, such as the spinal nerve. While a considerable improvement over the existing procedures, nevertheless, this procedure does not enable the surgeon to directly view the resection of posterior nuclear fragments. That is, the internal diameter of the access cannula as described in U.S. Pat. No. 4,573,448 limits the design of an operating discoscope and limits the type and size of instruments that would allow for the visualization and simultaneous suction, irrigation and resection of the nuclear material.

The introduction of a second portal to the annulus from the opposite side of a first portal has been reported by Schreiber and his co-workers in *Clinical Orthopaedics and Related Research*, Number 238, page 36, January 1989. However, this bilateral, biportal procedure increases the operating room time, exposure to radiation by physician, patient and operating room personnel and also increases post-operative morbidity by involving both sides of the back and may cause excessive removal of nuclear material which increases the possibility for stenosis of the foramen and nerve root compression.

Thus, there is a need in the art for a percutaneous procedure to create an accessory unilateral portal in the annulus adjacent to an already positioned access cannula with a minimal additional exposure of the patient, physician and operating room staff to radiation and without unduly prolonging time spent in the operating room. A unilateral, biportal approach will allow for continuous visualization, identification and extraction of nuclear fragments from the disc under discoscopic control. Large central herniations and partially extruded fragments may be visualized and evacuated. Such a unilateral approach to place more than one percutaneous portal in, for example, the L5-S1 vertebral joint, is also highly desirable because this procedure requires deflection of the patient's spine to enable access on the one side, causing a corresponding restriction of access on the opposite side. Moreover, by using a unilateral biportal approach, instruments do not need to traverse across the disc nucleus from a second portal remote from the symptomatic side. Therefore, the amount of non-symptomatic nuclear material removed by the unilateral approach is decreased as compared to the bilateral, biportal approach. This is important in preventing collapse of disc space, which results in nerve compression and stenosis of the spinal canal. Also, another significant benefit of the unilateral approach is that the musculature and soft tissue and disc are traumatized on only one side of the back.

The present invention provides a percutaneous surgical disc procedure, comprising the steps of percutaneously entering the back of the patient in a posterolateral direction with an access cannula, advancing said access cannula through a first percutaneously created fenestration of the annulus of the disc, percutaneously entering the back of the patient in a posterolateral direction with an accessory cannula, and advancing said accessory cannula through a second percutaneously created fenestration of the annulus adjacent to and on the same side of the disc as the first fenestration.

The present invention also provides a method for the percutaneous decompression of a herniated intervertebral disc in a human patient, which comprises percutaneously entering the back of the patient in a posterolateral direction with an access cannula, advancing the access cannula into the disc through a first percutaneously created fenestration of the annulus of the disc, percutaneously entering the back of the patient in a posterolateral direction with an accessory cannula, advancing the accessory cannula into the disc through a second percutaneously created fenestration of the annulus adjacent to and on the same side of the disc as the first fenestration, removing nuclear material through one of the cannulae and observing the removal with an endoscope through the other cannula.

In a broader sense, the present invention provides a method of percutaneously emplacing at least two cannulae in a patient, comprising percutaneously entering the back of the patient in a posterolateral direction with a first cannula and advancing the first cannula into the body of the patient to a position where the distal end of the first cannula is at a first predetermined location inside the body and the proximal end thereof projects beyond the outer surface of the back, securing a guide means to the proximal end of the first cannula and using the guide means to guide a second cannula as it percutaneously enters the back of the patient in a posterolateral direction and is advanced to a second predetermined location relative to said first predetermined location.

The method of the present invention requires only a small incision to place the cannulae, since this biportal approach utilizes unilateral placement The unilateral biportal approach allows for continuous discoscopic control and visualization and provides adequate channels for fluid management, which significantly enhances the visual identification of the posterior annulus. The method in accordance with the invention may be carried out under local anesthesia, thus avoiding the risk of general anesthetics.

The present invention is illustrated in terms of its preferred embodiments in the accompanying drawings, in which:

FIG. 1 is a plan view of a guide wire useful in the present invention;

FIG. 2 is a plan view, partly in section, of a cannulated obturator useful in the present invention;

FIG. 3 is a plan view, partly in section, of an access cannula useful in the present invention;

FIG. 4 is a plan view of a trephine useful in the present invention;

FIG. 5 is an elevational view of a first jig useful in the present invention;

FIG. 6 is a view in section, taken along lines 6—6 in FIG. 5;

FIG. 7 is an elevational view in section of a sealing adaptor useful in the present invention;

FIG. 8 is an elevational view of a second jig useful in the present invention;

FIG. 9 is a view in section, taken along the lines 9—9 in FIG. 8;

FIG. 10 is a schematic view of a first access cannula inserted into the herniated disc;

Figure 11:
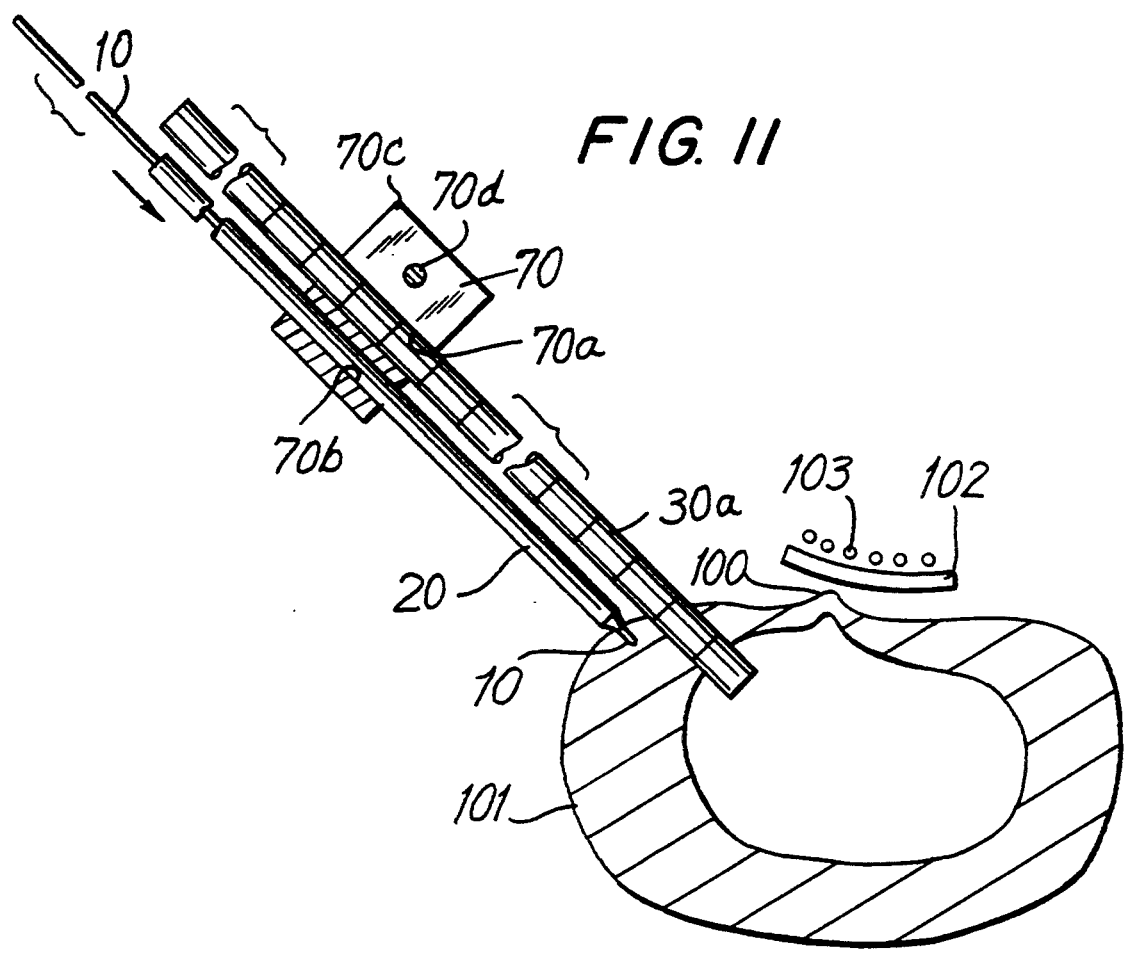
FIG. 11 is a view similar to FIG. 10 showing the use of the second jig to index a second access cannula relative to the first access cannula.

In the description that follows, instruments are generally made out of suitable austenitic stainless steel, unless otherwise specified. While the surgical procedure described herein refers to decompression of intervertebral lumbar discs, it is to be understood that the procedure is not limited to lumbar discectomy and may be used in any procedure for percutaneously emplacing at least two cannulae in a patient, such as an intervertebral disc procedure or operation.

According to the method of the present invention, the patient is positioned on a radiolucent table in the appropriate prone or lateral position and a guidewire 10 (FIG. 1), suitably of about 0.050 in. diameter, is advanced through the skin of the back posterolaterally under fluoroscopic observation until the guidewire 10 contacts the exterior symptomatic side of the annulus fibrosis of the herniated disc. Thereafter, the cannulated obturator 20 (FIG. 2), having a lumen with a diameter slightly larger than that of the guidewire 10, is passed over the guidewire 10 until the cannulated obturator 20 contacts the external surface of the annulus fibrosis of the herniated disc. The removal of the guidewire 10 at this point is optional. An access cannula 30a (FIG. 3), suitably of about 0.25 in. outer diameter and having external gradations 31 of 10 mm, is then passed over the cannulated obturator 20 and advanced to the external surface of the annulus fibrosis. At this point, the guidewire 10 is removed if not previously removed. The inner diameter of the access cannula 30a is sized to closely fit over the cannulated obturator 20. The cannulated obturator 20 is then removed, and a 3 mm or 5 mm trephine 40 (FIG. 4) is introduced through the access cannula 30a. The trephine 40 has a plurality of saw teeth 40a or other cutting members. The trephine 40 is advanced into the annulus of the disc, with rotation, creating an annular fenestration (that is, a bore) through the annulus fibrosis into the nucleus. The trephine 40 is then removed.

The cannulated obturator 20 is reintroduced into the access cannula 30a and passed into the fenestration of the annulus. Fluoroscopic guidance may be utilized. The access cannula 30a is then advanced into the fenestration of the annulus, with rotary movement. After the access cannula 30a is in the proper position, the cannulated obturator 20 is removed. The proximal end of cannula 30a projects beyond the surface of the patient's back (not shown) while the distal end is in the position shown in FIG. 10. The procedure described for placement of cannula 30a into the annulus of the disc follows the procedure described in U.S. Pat. No. 4,573,448. As is known, suitable local anesthetic is used as appropriate.

Referring to FIG. 10, the procedure described above locates the distal end of the access cannula 30a adjacent the herniation 100 of the disc 101, which protrudes toward the posterior ligament 102 thus placing pressure on the nerves 103, which causes the pain characteristic of a herniated lumbar disc. First jig 50 (FIGS. 5, 6 and 10) is slid downwardly over the proximal end of the access cannula 30a by passing the access cannula 30a through the central bore 51 in the first jig 50. Jig 50 is secured in place near the proximal end of cannula 30a by tightening the screw 53 thereby clamping the legs 52a and 52b to the access cannula 30a.

First jig 50 preferably has a plurality of smaller bores 55 each having a diameter substantially the same as the diameter of the guidewire 10. The axes of the bores 55 are spaced from and are preferably parallel to the axis of the large bore 51. Alternatively, jig 50 may have only one smaller bore 55. Moreover, the bores 55 may be oblique to the axis of the large bore 51.

Under fluoroscopic observation, the guidewire 10 is slid through a selected one of the small bores 55 so that the guidewire 10 will ideally be centered on the annulus fibrosis. If necessary, a second guidewire 10 is passed through another of bores 55 and advanced toward the annulus fibrosis of the disc, while under fluoroscopic observation. Proper positioning of the guidewire on the annulus is determined by palpation and, if necessary, by fluoroscopy. The surgeon can then evaluate the placement of the guidewires and select the guidewire best positioned to provide the second fenestration of the annulus of the disc.

Having selected the desired guidewire 10, the other guidewire, if any, is removed, and the guidewire 10 is then introduced through the fibers of the annulus fibrosis for a distance of about three to about four millimeters. Jig 50 is removed, leaving the guidewire 10 and access cannula 30a in place.

Second jig 70 (FIGS. 8, 9 and 11) is secured to access cannula 30a near the proximal end by passing access cannula 30a through bore 70a, passing the guidewire 10 through bore 70b, and clamping legs 70c together by means of screw 70d. Cannulated obturator 20 is then advanced over the guidewire 10 by rotary movement through the bore 70b of the second jig 70 until the cannulated obturator 20 contacts the annulus fibrosis, as shown in FIG. 11. The guidewire 10 and jig 70 are removed leaving the cannulated obturator 20 in place. An accessory cannula 30b is passed over the cannulated obturator 20 and advanced toward the annulus fibrosis. Accessory cannula 30b is sized to slide in the annulus between bore 70b and the outer surface of cannulated obturator 20. The cannulated obturator 20 is then removed, leaving the accessory cannula 30b in place.

Although it is presently preferred to use second jig 70, it is not necessary to do so. Moreover, while the bores 70a and 70b are presently preferred to be parallel, in some cases it may be desired to have one bore oblique to the other. Also, while it is presently preferred that cannulae 30a, 30b have the same inner and outer diameters, one may have a smaller inner and/or outer diameter than the other.

The annulus fibrosis is inspected endoscopically through the accessory cannula 30b, and if satisfactory, a trephine 40 is passed through the accessory cannula 30b and a second fenestration is cut through the annulus fibrosis into the nucleus. The trephine 40 is then removed. The accessory cannula 30b is advanced into the annulus. Introduction of both cannulae into the annulus of the disc under fluoroscopic observation is carried out in a manner known per se, such as described in U.S. Pat. No. 4,573,448.

Fragments of the herniated disc can be removed through the desired cannula 30a or 30b by inserting a trephine 40 in the desired cannula and moving it back and forth within the nucleus of the herniated disc as suction is applied. Alternatively, the trephine can be removed and suction may be applied through the cannula itself. In another method, forceps, trimmer blades, suction punch forceps, laser lights, etc. are used to remove such fragments via one of the cannula.

Figure 12:
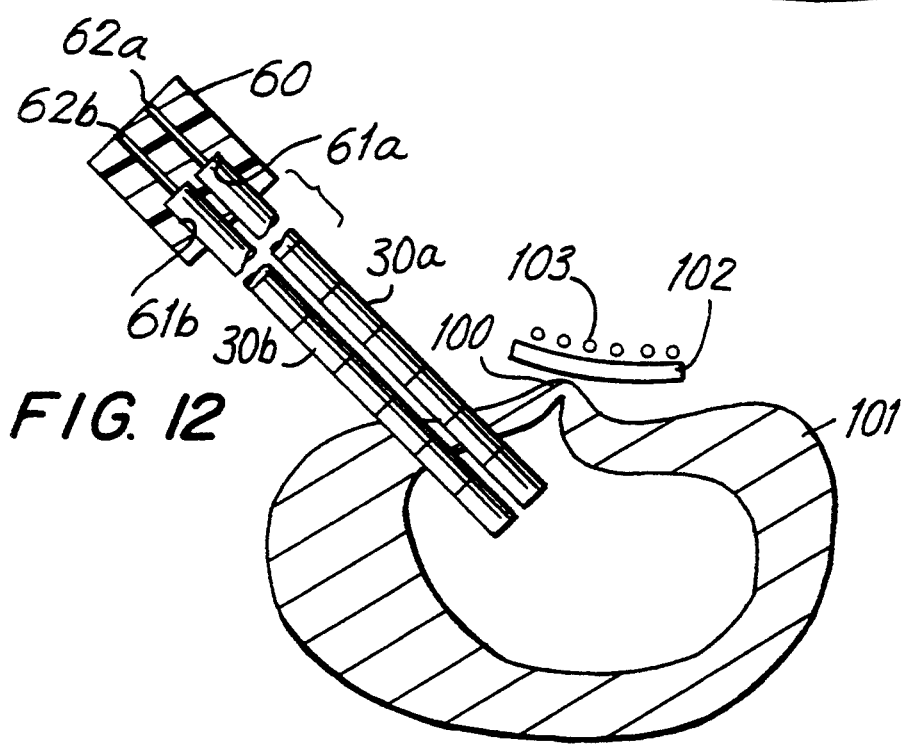
FIG. 12 is a schematic view showing two access cannulae placed in the body of the patient.

Preferably, however, before removal of nuclear material, a sealing adaptor 60 (FIG. 7), which is suitably comprised of silicon rubber, is attached to the proximal extremity of the access cannula 30a and accessory cannula 30b, as shown in FIG. 12 with access cannula 30a and accessory cannula 30b received in bores 61a and 61b of sealing adaptor 60. Insertion of access cannula 30a and accessory cannula 30b into the sealing adaptor will stop when the cannulae contact shoulders 63 and 64, respectively of bores 61a and 61b. Nuclear evacuation through one of the cannulae 30a or 30b and simultaneous arthroscopic observation via the other of cannulae 30a or 30b is possible by sealingly passing an arthroscope (not shown) into one of bores 62a and 62b and thence into one of cannulae 30a or cannula 30b, while a tool (not shown) is inserted into the other bore and thence into the other cannula. Nuclear material may then be evacuated by a conventional powered surgical instrument (not shown) through the access cannula 30a or accessory cannula 30b while under arthroscopic observation through the other cannula. A saline solution may be passed via the arthroscope through one cannula and excess fluid may be evacuated through the other cannula. Direct visualization of the resection of the desired disc material is thus made possible.

I claim:

1. A percutaneous surgical disc procedure, comprising the steps of:
   a) percutaneously entering the back of the patient in a posterolateral direction with an access cannula;
   b) advancing said access cannula through a first percutaneously created fenestration of the annulus of the disc;
   c) securing a guide means to said access cannula and orienting an accessory cannula relative to the guide means to guide said accessory cannula;
   d) percutaneously entering the back of the patient in a posterolateral direction with said accessory cannula;
   e) advancing said accessory cannula through a second percutaneously created fenestration of the annulus adjacent to and on the same side of the disc as the first fenestration so that the access cannula and the accessory cannula are oriented relative to each other on the same side of the disc.

2. The procedure according to claim 1, wherein a surgical tool is operated through one of said cannulae.

3. The procedure according to claim 2, wherein the operation of said surgical tool is observed through the other of said cannulae.

4. A method for the decompression of a herniated intervertebral disc in a human patient, comprising the steps of:
   a) percutaneously entering the back of the patient in a posterolateral direction with an access cannula;
   b) advancing said access cannula into the disc through a first percutaneously created fenestration of the annulus of the disc;
   c) securing a guide means to said access cannula and orienting an accessory cannula relative to the guide means to guide said accessory cannula;
   d) percutaneously entering the back of the patient in a posterolateral direction with said accessory cannula;
   e) advancing said accessory cannula into the disc through a second percutaneously created fenestration of the annulus adjacent to and on the same side of the disc as the first fenestration so that the access cannula and the accessory cannula are oriented relative to each other on the same side of the disc;
   f) removing nuclear material from one of the cannulae and observing the removal with an endoscope through the other cannula.

5. A method for the decompression of a herniated intervertebral disc in a human patient, comprising the steps of:
   a) percutaneously entering the back of the patient in a posterolateral direction with an access cannula;
   b) advancing said access cannula into the disc through a first percutaneously created fenestration of the annulus of the disc, said access cannula having a distal end within said disc and a proximal end projecting beyond the surface of the patient's back;
   c) securing a first jig means to said access cannula's proximal end, said first jig means having at least one small bore therethrough;

d) sliding a guidewire through said bore and embedding said guidewire into the annulus fibrosis of said disc;
e) removing said jig means from said access cannula;
f) percutaneously entering the back of the patient in a posterolateral direction with an accessory cannula;
g) advancing said accessory cannula, with the use of said embedded guidewire, into the nucleus of the disc through a second percutaneously created fenestration of the annulus adjacent to and on the same side of the disc as the first fenestration;
h) removing nuclear material from one of the cannulae; and
i) observing the removal with an endoscope through the other cannula.

6. A method for the decompression of a herniated intervertebral disc in a human patient, comprising the steps of:
a) percutaneously entering the back of the patient in a posterolateral direction with an access cannula;
b) advancing said access cannula into the disc through a first percutaneously created fenestration of the annulus of the disc, said access cannula having a distal end within said disc and a proximal end projecting beyond the surface of the patient's back;
c) securing a first jig means to said access cannula's proximal end, said first jig means having a plurality of small bores therethrough arranged with their axes parallel to one another and, when said first jig means is attached to said access cannula, spaced from and parallel to the axis of said access cannula;
d) sliding a guidewire through a selected one of said bores and embedding said guidewire into the annulus fibrosis of said disc;
e) removing said jig means from said access cannula;
f) percutaneously entering the back of the patient in a posterolateral direction with an accessory cannula;
g) advancing said accessory cannula, with the use of said embedded guidewire, into the nucleus of the disc through a second percutaneously created fenestration of the annulus adjacent to and on the same side of the disc as said access cannula;
h) removing nuclear material from one of the cannulae; and
i) observing the removal with an endoscope through the other cannula.

7. The method according to claim 6, wherein after said first jig means is removed from said access cannula, a cannulated obturator is percutaneously advanced to said disc by sliding said cannulated obturator over said guidewire, said accessory cannula is percutaneously advanced to said disc by sliding said accessory cannula over said cannulated obturator, and after removal of said embedded guidewire and said cannulated obturator, a fenestration is created in said annulus fibrosis via said accessory cannula and said accessory cannula is percutaneously advanced through said fenestration into the nucleus of said disc on the same side of said disc as said access cannula.

8. The method according to claim 7, wherein after said first jig means is removed from said access cannula, a second jig means having a bore therethrough is secured to said access cannula proximal end with said guidewire passing through said bore of said second jig means at least substantially parallel to the axis of said accessory cannula, and thereafter said cannulated obturator and said accessory cannula are each advanced through said bore of said second jig means to said disc and said nucleus, respectively.

* * * * *